(12) United States Patent
Teichmann et al.

(10) Patent No.: US 10,414,783 B2
(45) Date of Patent: Sep. 17, 2019

(54) CHLOROSILYLARYLGERMANES, METHOD FOR PREPARATION THEREOF AND USE THEREOF

(71) Applicant: Evonik Degussa GmbH, Essen (DE)

(72) Inventors: Julian Teichmann, Frankfurt am Main (DE); Matthias Wagner, Niddatal (DE); Hans-Wolfram Lerner, Oberursel (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/994,110

(22) Filed: May 31, 2018

(65) Prior Publication Data

US 2018/0346494 A1    Dec. 6, 2018

(30) Foreign Application Priority Data

Jun. 1, 2017  (EP) .................................. 17173940

(51) Int. Cl.
| | | |
|---|---|---|
| H01L 21/205 | (2006.01) | |
| C07F 7/30 | (2006.01) | |
| H01L 21/02 | (2006.01) | |

(52) U.S. Cl.
CPC .......... *C07F 7/30* (2013.01); *H01L 21/02532* (2013.01); *H01L 21/02628* (2013.01); *H01L 21/2053* (2013.01); *C07B 2200/13* (2013.01)

(58) Field of Classification Search
CPC ........... H01L 21/02532; H01L 21/0262; H01L 21/02628; H01L 21/2053; H01L 21/208; C07F 7/14; C07F 7/30

See application file for complete search history.

(56) References Cited

U.S. PATENT DOCUMENTS

| | | | |
|---|---|---|---|
| 7,540,920 B2 | 6/2009 | Singh et al. | |
| 2004/0194703 A1* | 10/2004 | Shenai-Khatkhate | ...................... C07C 391/00 118/715 |
| 2004/0197945 A1* | 10/2004 | Woelk | ................... C07F 7/0807 438/99 |
| 2010/0151666 A1 | 6/2010 | Kouvetakis et al. | |
| 2014/0178284 A1* | 6/2014 | Lang | ..................... C01B 33/107 423/342 |
| 2017/0243742 A1* | 8/2017 | Takahashi | ......... H01L 21/02647 |

FOREIGN PATENT DOCUMENTS

| | | |
|---|---|---|
| WO | WO 2004/036631 A2 | 4/2004 |
| WO | WO 2009/005862 A2 | 1/2009 |

OTHER PUBLICATIONS

Lars Müller, et al., "Trichlorosilylation of chlorogermanes and chlorostannanes with $HSiCl_3/Net_3$ followed by base-catalysed formation of $(Me_3Ge)_2Si(SiCl_3)_2$ and related branched stannylsilanes", Journal of Organometallic Chemistry, vol. 579, 1999, pp. 156-163.

(Continued)

*Primary Examiner* — Stephen W Smoot
(74) *Attorney, Agent, or Firm* — Oblon, McClelland, Maier & Neustadt, L.L.P.

(57) ABSTRACT

A novel compound chlorosilylarylgermane, a method for preparing the compound, and the use of the compound are described. A method for preparing trichlorosilyltrichlorogermane and the use of trichlorosilyltrichlorogermane are also described.

14 Claims, 6 Drawing Sheets

(56) References Cited

OTHER PUBLICATIONS

Jesse B. Tice, et al., "Synthesis and Fundamental Properties of Stable $Ph_3SnSiH_3$ and $Ph_3SnGeH_3$ Hydrides: Model Compounds for the Design of Si—Ge—Sn Photonic Alloys", Inorganic Chemistry, vol. 48, 2009, pp. 6314-6320.
Cole J. Ritter, et al., "Synthesis and Fundamental Studies of $(H_3Ge)_xSiH_{4-x}$ Molecules: Precursors to Semiconductor Hetero- and Nanostructures on Si", J. Am. Chem. Soc., vol. 127, 2005, pp. 9855-9864.
Thomas Lobreyer, et al., "Synthese und Struktur von Tetrasilylgerman, $Ge(SiH_3)_4$, und weiteren Silylgermanen", Angew. Chem., vol. 105, No. 4, 1993, pp. 587-588.
F. Fehér, et al., "Beiträge Zur Chemie Des Siliziums Und Germaniums XIV", Tetrahedron Letters, vol. 51, 1970, pp. 4443-4447.
Extended European Search Report dated Feb. 12, 2018 in Patent Application No. 17197538.6 (with English language translation of categories of cited documents).
Extended European Search Report dated Nov. 13, 2017 in Patent Application No. 17173940.2 (with English language translation of categories of cited documents).
U.S. Appl. No. 15/994,304, filed May 31, 2018, 2018/0346495, Teichmann, et al.

* cited by examiner

CHLOROSILYLARYLGERMANES, METHOD FOR PREPARATION THEREOF AND USE THEREOF

CROSS REFERENCE TO RELATED APPLICATION

This application claims the benefit of EP 17173940.2, filed Jun. 1, 2017, the entire disclosure of which is also incorporated herein by reference.

FIELD OF THE INVENTION

The present invention relates to novel chlorosilylarylgermanes, a method for preparation thereof and to the use thereof.

BACKGROUND

Halosilanes, polyhalosilanes, halogermanes, polyhalogermanes, silane, polysilanes, germane, polygermanes and corresponding mixed compounds have long been known, cf. in addition to the customary text books of inorganic chemistry also WO 2004/036631 A2 or C. J. Ritter et al., J. Am. Chem. Soc., 2005, 127, 9855-9864.

L. Müller et al. in J. Organomet. Chem., 1999, 579, 156-163 describe, inter alia, the preparation of trichlorosilylmethylgermanes.

Methylgermylsilanes and phenylgermylsilanes are known from Angew. Chem., 1993, 105, 587-588 (G. Sih et al.) and also from Tetrahedron Lett., 1970, 51, 4443-4447 (F. Feher et al.).

Furthermore, phenyl- and hydrogen-containing compounds are known in which Sn—Si and Sn—Ge bonds are present (J. B. Tice et al., J. Inorganic Chemistry, 2009, 48(13), 6314-6320). Here, it is suggested to use these compounds as IR semiconductors.

In patent document U.S. Pat. No. 7,540,920 B2, Singh et al. disclose Si—Ge compounds of the formula $X_1X_2X_3$—Si—Ge—$X_4X_5X_6$ having hydrogen or halogen radicals $X_{1-6}$.

Practically nothing is currently known about chlorosilylarylgermanes. Thus, by means of basic research, effort is being made to find novel compounds and to seek novel preparation routes, in particular also with respect to potential industrial and optionally improvable applications.

The object of the present invention is to provide novel silicon-germanium compounds and a method for the preparation thereof.

SUMMARY OF THE INVENTION

Surprisingly, new synthetic possibilities have been found for preparing silicon-germanium compounds, particularly $R_3Ge$—$SiCl_3$, $Cl_3Si$—$GeR_2$—$GeR_2$—$SiCl_3$,
$Cl_3Ge$—$SiCl_3$, $[Ph_4P][Ge(SiCl_3)_3]$, $[Ph_4P][Ge(SiCl_3)_3*GaCl_3]$, $[Ph_4P][Ge(SiCl_3)_3*BBr_3]$, by the reaction of chlorinated or perchlorinated, organic or inorganic germanium compounds of the type $R_nGeCl_{4-n}$ (n=0, 2, 3) with hexachlorodisilane with addition of catalytic amounts of an ammonium chloride salt $[R_4N]Cl$ or a phosphonium salt $[R_4P]Cl$ where the radicals R=Me, Et, iPr, nBu or with addition of stoichiometric amounts of such salts. By means of the reaction according to the invention, various silicon-germanium compounds are obtained.

In addition, it has been found that reactants of the type $R_3GeCl$ are converted by the reaction with $Si_2Cl_6$ in the presence of ammonium chloride, whereupon a Ge—Si bond is formed at the Ge—Cl position. In the reaction of $R_2GeCl_2$ with $Si_2Cl_6$/ammonium chloride, the Ge—Si bond formation takes place at only one Ge—Cl position. In addition, Ge—Ge bond formation occurs at the second Ge—Cl position. The germanium-silicon compounds thus found or prepared can be converted with $LiAlH_4$ to silicon hydride compounds. In the context of the present invention, such compounds are prepared by the synthesis of $Ph_3Ge$—$SiH_3$ from $Ph_3Ge$—$SiCl_3$ for example. In the case of reactions of compounds of the type $R_nGeCl_{4-n}$ (n=0), different reactions take place depending on the stoichiometry.

[$R_4N$][$GeCl_3$] salts ($GeCl_4$:$Si_2Cl_6$:[$R_4N$]Cl, 1:1:1), $Cl_3Si$—$GeCl_3$($GeCl_4$:$Si_2Cl_6$:[$R_4N$]Cl, 1:1:0.1), or

[$Ph_4P$][$Ge(SiCl_3)_3$]($GeCl_4$:$Si_2Cl_6$:[$Ph_4P$]Cl, 1:4:1)

were produced. [$Ph_4P$][$Ge(SiCl_3)_3$] can be reacted with Lewis acids, abbreviated to "LA", to give the corresponding adducts [$Ph_4P$][$Ge(SiCl_3)_3*LA$].

DETAILED DESCRIPTION OF THE INVENTION

In the context of the invention, the measure "equivalent", "eq." for short, is understood to mean the amount of catalyst in mol based on the amount of hexachlorodisilane in mol. For example, 0.1 eq of catalyst denotes 0.1 mol of catalyst per mole of hexachlorodisilane or 10 mol % of catalyst based on hexachlorodisilane.

In the context of the invention, "hexachlorodisilane" is also abbreviated to "HCDS".

The present invention therefore provides chlorosilylarylgermanes of the general formula (I)

$XGe(Y_2)$—$SiCl_3$ (I), where X=Y or X=[—$Ge(Y_2)$—$SiCl_3$] and the Y groups are each independently phenyl (Ph).

The subject matter is also a method for preparing a chlorosilylarylgermane according to the invention, by
(a) dissolving an arylchlorogermane with hexachlorodisilane in a solvent and (b) reacting in the presence of a catalyst at a temperature of 5 to 40° C., wherein the aryl groups of the arylchlorogermane are each independently phenyl.

The invention is elucidated in more detail hereinafter.

The chlorosilylarylgermanes according to the invention can be selected from the series comprising trichlorosilyltriphenylgermane and/or 1,2-bis(trichlorosilyl)-1,1,2,2-tetraphenyldigermane.

In step (b) of the method according to the invention, it may be advantageous for the reaction to be carried out at room temperature.

Preferably, in step (a) of the method, a triarylchlorogermane may be used in a molar ratio to hexachlorodisilane of 1:1 and/or a diaryldichlorogermane may be used in a molar ratio to hexachlorodisilane of 1:2.

Furthermore, preference may be given to using an arylchlorogermane from the series comprising triphenylchlorogermane and/or diphenyldichlorogermane.

The solvent used in step (a) is preferably inert, selected to avoid undesired reactions with HCDS. Dichloromethane can particularly advantageously be used since this does not react with HCDS in the chosen temperature range.

It can also be advantageous when carrying out the method according to the invention to use phosphonium chlorides $[R_4P]Cl$ or ammonium chloride salts $[R_4N]Cl$ as catalyst, where the radicals R are selected from Me, Et, iPr, nBu, Ph. Preferably, R=nBu may be selected.

It has been observed that the reaction proceeds more slowly the less catalyst used. On the other hand, excessively large amounts of catalyst are undesirable since this has to be removed at the end of the reaction. It has been found that the method can be carried out economically with respect to the separation complexity if the catalyst is used in an amount of 0.001 to 1 mol per mole of hexachlorodisilane. The method is carried out particularly favourably if 0.01 to 0.1 mol is used per mole of hexachlorodisilane.

A further aspect of carrying out the method according to the invention economically is the selection of the amount of solvent. In the method, preferably at least 5 mol of solvent is used per mole of hexachlorodisilane, particularly preferably 10 mol to 100 mol of solvent per mole of hexachlorodisilane.

In the method according to the invention, it is advantageous to carry out the reaction with thorough mixing, preferably with stirring, and over a period of 1 to 24 hours, preferably over the course of 12 h, and further preferably under protective gas, preferably under nitrogen or argon, and subsequently to remove the solvent. This can be undertaken preferably in a dry oxygen-free environment, particularly preferably in an isolated environment, for example in a glove box, and further preferably at standard pressure or under reduced pressure, preferably in the range of 1 to 500 hPa, wherein chlorosilylarylgermanes formed are obtained as crystalline product.

Using the method according to the invention, the interesting molecule trichlorosilyltrichlorogermane can also be provided, which has already been disclosed by Singh et al. (U.S. Pat. No. 7,540,920 B2) without a method of preparation. For this purpose, the method is subjected to a simple modification, namely $GeCl_4$ is used instead of the arylchlorogermane. The conversion reaction with hexachlorodisilane is then subsequently carried out in a solvent and in the presence of a catalyst.

The invention therefore also relates to a method for preparing trichlorosilyltrichlorogermane by dissolving $GeCl_4$ with hexachlorodisilane in a solvent and reacting in the presence of a catalyst at a temperature of 5 to 40° C.

It can be advantageous to use the catalyst in amounts of 0.001 to 1 eq., preferably 0.01 to 0.1 eq. Example 3 describes an exemplary procedure of this method.

If this method is further modified by using the ammonium chloride salt $[R_4N]Cl$ or phosphonium chloride salt $[R_4P]Cl$ in a stoichiometric amount instead of a catalytic amount, preferably from 0.5 to 1.5 eq., particularly preferably 1 eq., then halogermanides are surprisingly obtained, for example trichlorogermanide on using $[R_4N]Cl$ or $[R_4P]Cl$. Example 4 describes a preferred procedure where R=Bu.

The synthesis carried out according to Example 4 presents a novel possibility of obtaining $[R_4N][GeCl_3]$ salts, by varying the cation $[R_4N]^+$ and by using the desired chloride salt for the heterolytic cleavage of $Si_2Cl_6$. This is particularly interesting since it has been found that the cation thus determines how well a compound crystallizes.

For instance, a large variety of $[R_4N][GeCl_3]$ and $[R_4P][GeCl_3]$ salts can be prepared in accordance with the invention. For example, in a preferred embodiment of this method, $[Ph_4P]^+$ may be used as cation in order to obtain tris(trichlorosilyl)germanide (Example 5). In addition, tris(trichlorosilyl)germanide may be reacted with $GaCl_3$. This is illustrated in Example 6.

In place of a reaction with $GaCl_3$, tris(trichlorosilyl)germanide can be reacted with $BBr_3$, which is illustrated by way of example in Example 7.

The Si—Ge compounds according to the invention or prepared in accordance with the invention may serve as precursors for materials which are used for the controlled deposition of thin Si—Ge layers.

The subject matter is also therefore the use of the chlorosilylarylgermane according to the invention or chlorosilylarylgermane prepared in accordance with the invention for generating Si—Ge layers.

Likewise, the subject matter is the use of the trichlorosilyltrichlorogermane prepared in accordance with the invention for generating Si—Ge layers.

Furthermore, the chlorosilylarylgermane according to the invention, the chlorosilylarylgermane prepared in accordance with the invention or the trichlorosilyltrichlorogermane prepared in accordance with the invention may be used preferably on conversion into the chlorinated form, into the hydrogenated form and/or on thermal decomposition thereof.

The examples which follow provide additional illustration of the present invention without restricting the subject matter. The term "room temperature" is abbreviated to "RT" in the examples.

Analytical Methods for Determination of the Crystal Structure

The data for all structures were collected at 173 K using a STOE IPDS II dual beam diffractometer using a Genix microfocus tube with mirror optics using $MoK_\alpha$ radiation ($\lambda$=0.71073 Å) and scaled using the frame scaling procedure of the X-AREA program (Stoe & Cie, 2002). The structures were solved by direct methods with the aid of the SHELXS program (Sheldrick, 2008) and refined on $F^2$ by the full matrix least squares technique. Cell parameters were determined by refinement on θ values of the reflections with $I > 6\sigma(I)$.

Input Materials:

Hexachlorodisilane, "HCDS" for short, $GeCl_4$ from Evonik Industries AG, triphenylchlorogermane, diphenyldichlorogermane.

Example 1: Preparation of Trichlorosilyltriphenylgermane (1)

The synthesis was carried out according to Equation 1 from $Ph_3GeCl$ and $Si_2Cl_6$ with addition of a catalytic amount of 0.1 eq of $[nBu_4N]Cl$.

Equation 1: Reaction of $Ph_3GeCl$ and $Si_2Cl_6$ with addition of a catalytic amount of 0.1 eq of $[nBu_4N]Cl$.

Figure 1A:
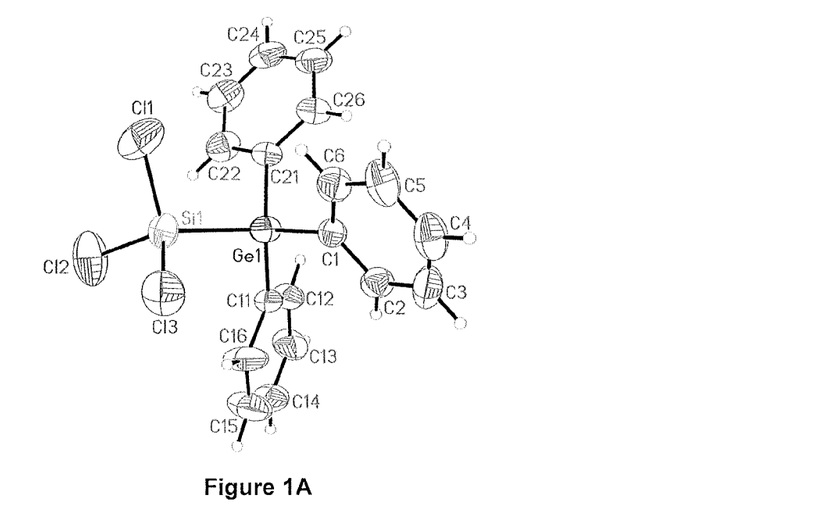
FIG. 1A shows the crystal structure of trichlorosilyltriphenylgermane.

To a clear colourless solution of 500 mg, corresponding to 1.47 mmol, of $Ph_3GeCl$ and 40 mg or 0.14 mmol of $[nBu_4N]Cl$ in 5 ml or 78.3 mmol of $CH_2Cl_2$ were added at room temperature while stirring 400 mg, corresponding to 1.49 mmol, of $Si_2Cl_6$. A clear colourless reaction solution was obtained which was stirred over the course of 12 h. A crude product in the form of a colourless crystalline solid 1 could be isolated from the reaction solution after slow removal of the solvent. The yield was 59%. The crude product still comprised up to about 30% of the reactant $Ph_3GeCl$. By means of X-ray diffractometric investigation, the crystal structure of 1 could be determined (FIG. 1A). Unmarked atoms in the figure represent hydrogen.

Figure 1B:
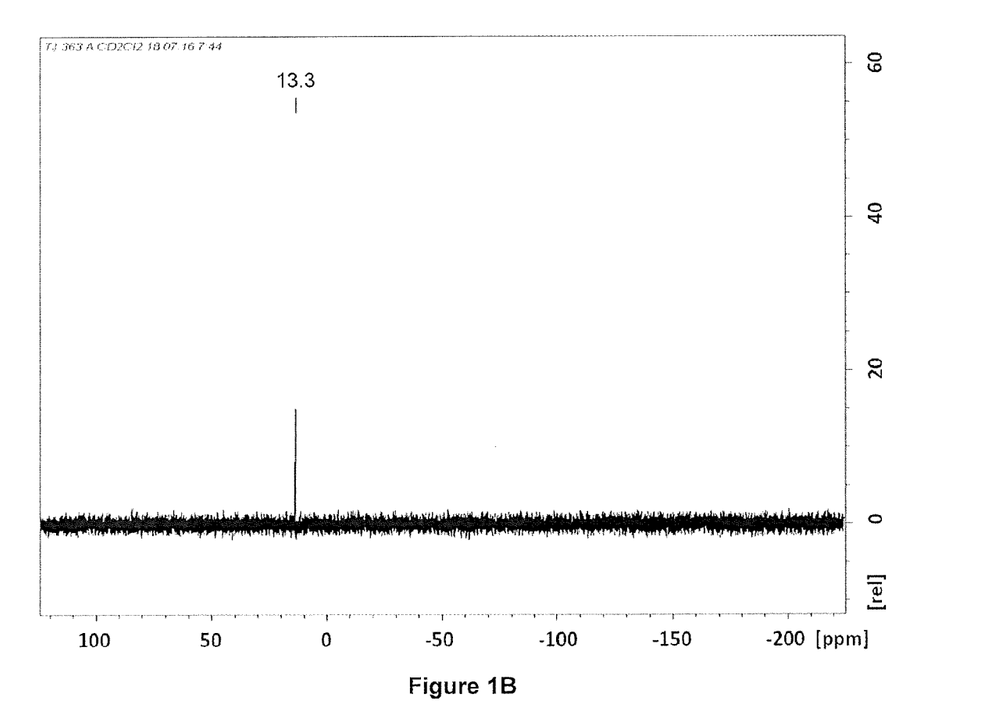
FIG. 1B shows the $^{29}$Si-NMR spectrum of the crude product of the synthesis of trichlorosilyltriphenylgermane.

The $^{29}Si$-NMR spectrum of 1 is shown in FIG. 1B.

All results of a $^1H$, $^{13}C$ and $^{29}Si$ NMR spectroscopic investigation:

$^{29}Si$ NMR (99.4 MHz, $CD_2Cl_2$, 298 K):
δ=13.3.

$^1H$ NMR (500.2 MHz, $CD_2Cl_2$, 298 K):
δ=7.58 (m); 7.75 (dd$^3$J(H,H)=8.0 Hz, $^2$J(H,H)=1.4 Hz).

$^{13}C$ NMR (125.0 MHz, $CD_2Cl_2$, 298 K):
δ=128.9; 130.1; 132.2; 135.3.

Example 2

Preparation of 1,2-Bis(Trichlorosilyl)-1,1,2,2-Tetraphenyldigermane (2).

The synthesis was carried out according to Equation 2 from $Ph_2GeCl_2$ and $Si_2Cl_6$ with addition of catalytic amounts (0.1 eq) of $[nBu_4N]Cl$.

Equation 2: Reaction of $Ph_2GeCl_2$ and $Si_2Cl_6$ with addition of catalytic amounts (0.1 eq) of $[nBu_4N]Cl$.

To a clear colourless solution comprising 500 mg or 1.68 mmol of $Ph_2GeCl_2$ and 90 mg or 0.17 mmol of $[nBu_4N]Cl$ in 5 ml or 78.3 mmol of $CH_2Cl_2$ were added at room temperature 903 mg or 3.36 mmol of $Si_2Cl_6$. The resulting reaction solution was subsequently stirred at room temperature over the course of 12 h.

Figure 2:
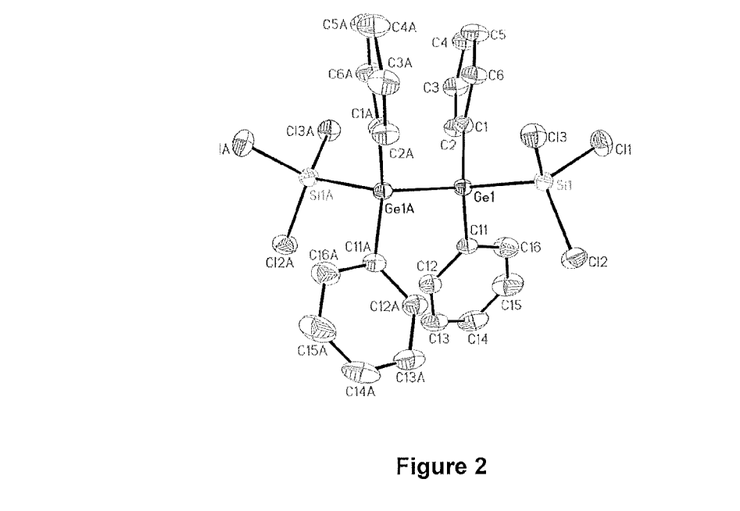
FIG. 2 shows the crystal structure of 1,2-bis(trichlorosilyl)-1,1,2,2-tetraphenyldigermane.

A crude product could be obtained in a yield of 77% from the reaction solution by slow removal of the solvent which, by extraction with $Et_2O$ and subsequent crystallization, could be isolated as a colourless crystalline solid 2. The yield in this case was 57%. By means of X-ray diffractometry, the crystal structure of 2 could be determined, shown in FIG. 2.

All results of a $^1H$, $^{13}C$ and $^{29}Si$ NMR spectroscopic investigation:

$^{29}Si$ NMR (99.4 MHz, $CH_2Cl_2$, 298 K):
δ=12.3

$^1H$ NMR (500.2 MHz, $CH_2Cl_2$, 298 K):
δ=7.41 (t$^3$J(H,H)=7.2 Hz (2H)), 7.47 (d$^3$J(H,H)=7.2 Hz (1H)), 7.56 (d$^3$J(H,H)=7.2 Hz (2H)).

$^{13}C$ NMR (125.0 MHz, $CH_2Cl_2$, 298 K):
δ=129.0; 130.1; 131.8; 136.0.

Example 3: Preparation of Trichlorosilyltrichlorogermane (3)

The synthesis was effected according to Equation 3 from $GeCl_4$ and $Si_2Cl_6$ (1:1) with addition of 0.1 eq. of $[nBu_4N]Cl$ as a catalytic amount.

Equation 3: Reaction of $GeCl_4$ and $Si_2Cl_6$ (1:1) with addition of a catalytic amount (0.1 eq.) of the catalyst where R = Bu: $[nBu_4N]Cl$.

To a clear colourless solution comprising 100 mg or 0.4 mmol of $[nBu_4N]Cl$ in a 30:70 mixture of $GeCl_4$ and $CH_2Cl_2$ was added at room temperature 1 g or 3.7 mmol of $Si_2Cl_6$ and the reaction mixture thus obtained was stirred at room temperature over the course of 12 h. The product 3 was condensed with other volatile constituents from the reaction solution into a nitrogen-cooled receiver. Subsequent distillation at 1013 hPa resulted in the isolation of pure 3 as a clear colourless liquid in a yield of 22%.

Figure 3:
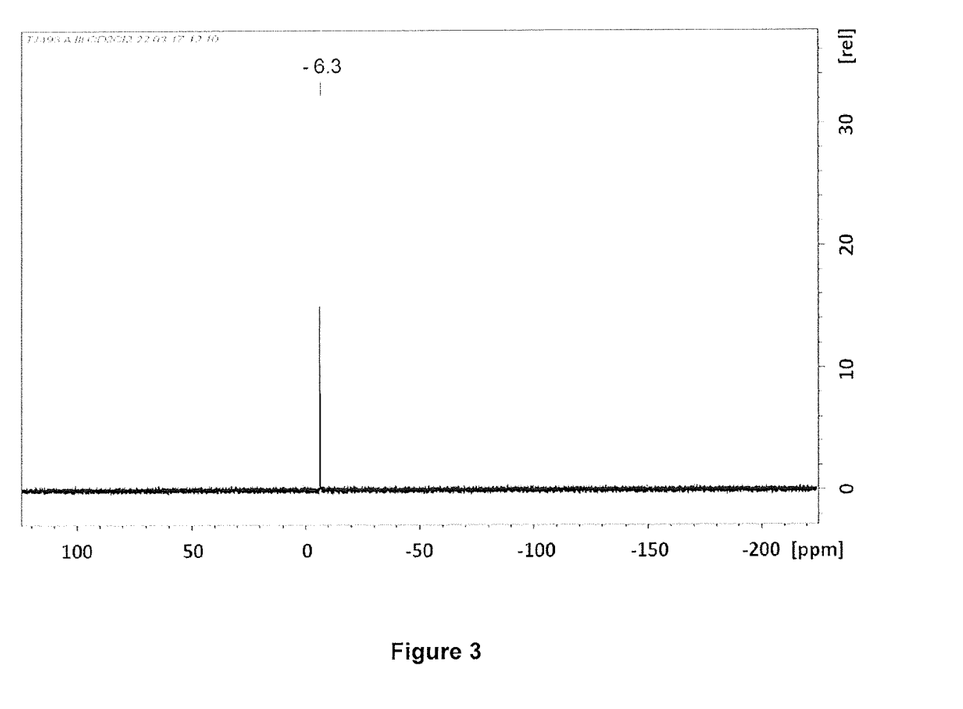
FIG. 3 shows the $^{29}$Si-NMR spectrum of trichlorosilyltrichlorogermane.

The $^{29}Si$-NMR spectrum of 3 is shown in FIG. 3.

All results of a $^{29}Si$-NMR spectroscopic investigation:

$^{29}Si$ NMR (99.4 MHz; $CH_2Cl_2$; 298 K):
δ=6-6.3.

Example 4: Preparation of Trichlorogermanide (4)

The procedure was as in Example 3 but with the difference that $[nBu_4N]Cl$ was used in a stoichiometric amount synonymous to 1 eq.

The conversion reaction was effected in a redox reaction according to Equation 4.

Equation 4: Reaction of $GeCl_4$ and $Si_2Cl_6$ (1:1) with addition of a stoichiometric amount, namely 1 eq. of $[nR_4N]Cl$ where R = Bu.

Figure 4:
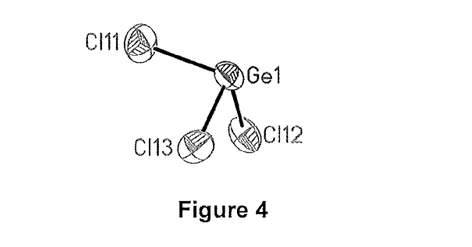
FIG. 4 shows the crystal structure of trichlorogermanide.

To a clear colourless solution of 300 mg or 1.4 mmol of $GeCl_4$ and 390 mg or 1.4 mmol of $[nBu_4N]Cl$ in $CH_2Cl_2$ were added at room temperature 375 mg or 1.4 mmol of $Si_2Cl_6$ and the reaction mixture thus obtained was stirred at room temperature over the course of 12 h. Trichlorogermanide 4 could be isolated from the reaction solution as a yellow crystalline solid after slow removal of the solvent. By means of X-ray diffractometry, the structure of 4 could be

Example 5: Preparation of Tris(Trichlorosilyl)Germanide (5)

The synthesis was effected according to Equation 5 from GeCl$_4$ and Si$_2$Cl$_6$ in a molar ratio of 1:4 with addition of a stoichiometric amount, in this case 1 eq., of [Ph$_4$P]Cl.

Equation 5: Reaction of GeCl$_4$ and Si$_2$Cl$_6$ (1:4) with addition of a stoichiometric amount (1 eq.) of [Ph$_4$P]Cl.

Figure 5A:
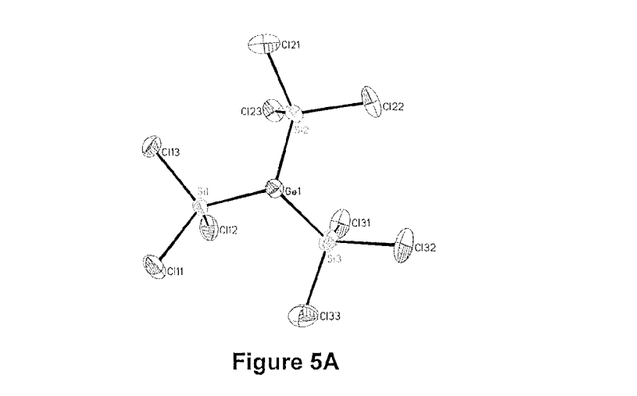
FIG. 5A shows the crystal structure of tris(trichlorosilyl)germanide.

To a clear colourless solution comprising 93 mg or 0.4 mmol of GeCl$_4$ and 163 mg or 0.4 mmol of [Ph$_4$P]Cl in CH$_2$Cl$_2$ as solvent were added at room temperature 478 mg or 1.7 mmol of Si$_2$Cl$_6$ and the reaction mixture thus obtained was stirred at room temperature over the course of 12 h. 5 could be isolated in 99% yield from this mixture as a yellow crystalline solid after slow removal of the solvent. By means of X-ray diffractometry, the crystal structure of 5 could be determined, shown in FIG. 5A. For reasons of clarity, the cation [Ph$_4$P]$^+$ is not depicted here.

In this reaction there is a reduction of the GeCl$_4$ and a threefold silylation of the germanium atom takes place.

Figure 5B:
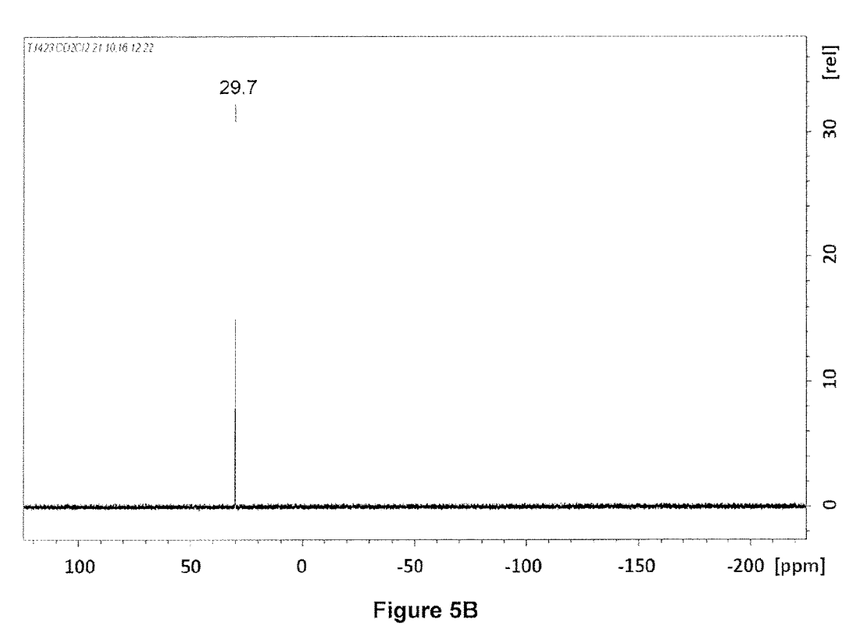
FIG. 5B shows the $^{29}$Si-NMR spectrum of tris(trichlorosilyl)germanide.

The $^{29}$Si-NMR spectrum of 5 is shown in FIG. 5B.

All results of a $^1$H- and $^{29}$Si-NMR spectroscopic investigation:

$^{29}$Si NMR (99.4 MHz; CD$_2$Cl$_2$; 298 K):
δ=29.7.

$^1$H NMR (500.2 MHz; CD$_2$Cl$_2$; 298 K):
δ=7.54 (qd$^3$J(H,H)=4.5 Hz; $^2$J(H,H)=1.3 Hz; (2H)); 7.68 (td$^3$J(H,H)=7.4 Hz; $^3$J(H,H)=3.4 Hz (2H)); 7.84 (tt$^3$J(H, H)=7 Hz; $^2$J(H,H)=1.0 Hz (1H)).

Example 6: Preparation of Tris(Trichlorosilyl)Germanide Adduct of GaCl$_3$ (6)

The synthesis of 6 was effected according to Equation 6 from tris(trichlorosilyl)germanide (5) and GaCl$_3$.

Equation 6: Reaction of 5 with GaCl$_3$.

Figure 6A:
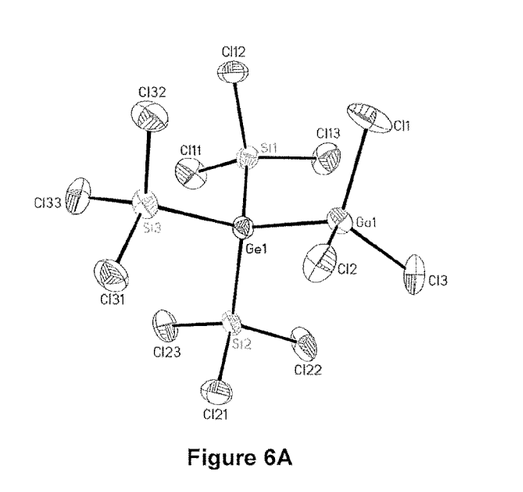
FIG. 6A shows the crystal structure of tris(trichlorosilyl)germanide adduct of $GaCl_3$.

50 mg or 0.1 mmol of 5 and 10 mg or 0.1 mmol of GaCl$_3$ were mixed as solids at room temperature and subsequently dissolved completely in CH$_2$Cl$_2$. The clear yellow reaction mixture was stirred at room temperature over the course of 12 h. 6 could be obtained from the clear yellow reaction solution as a yellow crystalline solid in a yield of 82% by slow removal of the solvent. By means of X-ray diffractometry, the crystal structure of 6 could be determined, shown in FIG. 6A. For reasons of clarity, the cation [Ph$_4$P]$^+$ is not depicted here.

Figure 6B:
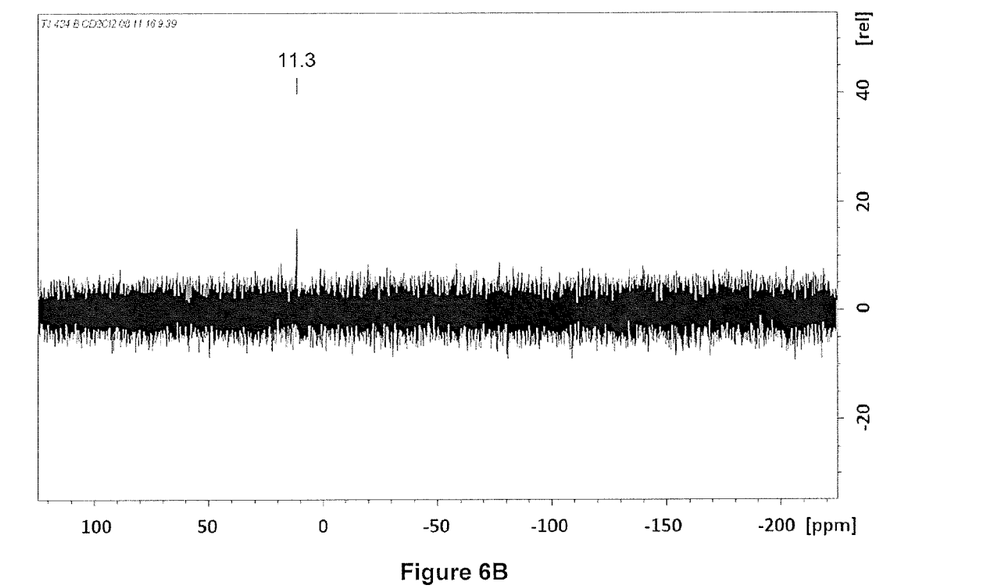
FIG. 6B shows the $^{29}$Si-NMR spectrum of the tris(trichlorosilyl)germanide adduct of $GaCl_3$.

The $^{29}$Si-NMR spectrum of 6 is shown in FIG. 6B.

All results of a $^1$H- and $^{29}$Si-NMR spectroscopic investigation:

$^{29}$Si NMR (99.4 MHz; CD$_2$Cl$_2$; 298 K):
δ=11.3.

$^1$H NMR (500.2 MHz; CD$_2$Cl$_2$; 298 K):
δ=7.54 (qd$^3$J(H,H)=4.5 Hz; $^2$J(H,H)=1.3 Hz; (2H)); 7.68 (td$^3$J(H,H)=7.4 Hz; $^3$J(H,H)=3.4 Hz (2H)); 7.84 (tt$^3$J(H, H)=7 Hz; $^2$J(H,H)=1.0 Hz (1H)).

Example 7: Preparation of Tris(Trichlorosilyl)Germanide Adduct of BBr$_3$ (7)

The synthesis of 7 was effected according to Equation 7 from tris(trichlorosilyl)germanide (5) and BBr$_3$.

Equation 7: Reaction of 5 with BBr$_3$.

Figure 7A:
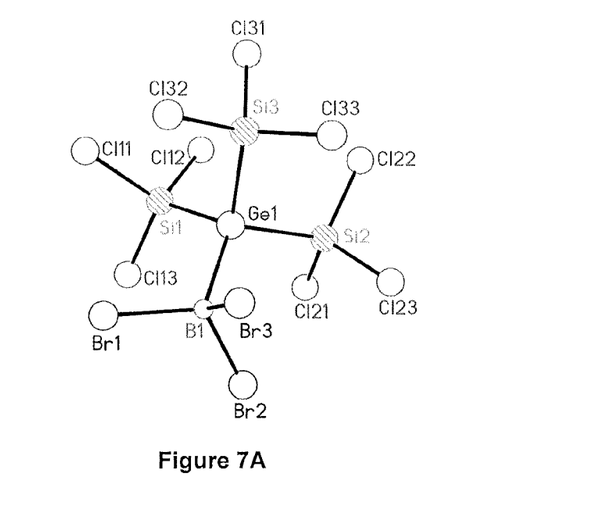
FIG. 7A shows the crystal structure of tris(trichlorosilyl)germanide adduct of $BBr_3$.

BBr$_3$ was added at room temperature to a clear yellow solution of 5 in CH$_2$Cl$_2$. After 4 days, colourless crystals had precipitated from the yellow reaction solution thus obtained. By means of X-ray diffractometry, the crystal structure of 7 could be determined, shown in FIG. 7A. For reasons of clarity, the cation [Ph$_4$P]$^9$ is not depicted here.

Figure 7B:
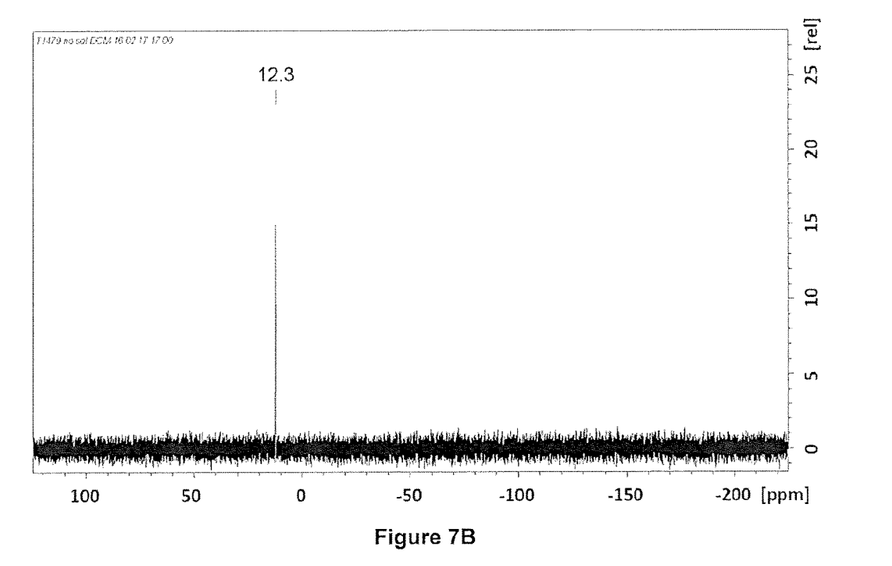
FIG. 7B shows the $^{29}$Si-NMR spectrum of the tris(trichlorosilyl)germanide adduct of $BBr_3$.

The $^{29}$Si-NMR spectrum of 7 is shown in FIG. 7B.

All results of a $^{11}$B- and $^{29}$Si-NMR spectroscopic investigation $^{29}$Si NMR (99.4 MHz; CD$_2$Cl$_2$; 298 K):
δ=12.3.

$^{11}$B NMR (160.5 MHz; CD$_2$Cl$_2$; 298 K):
δ=−17.5.

Numerous modification and variations on the present invention are possible in light of above teachings. It is therefore to be understood that within the scope of the appended claims, the invention may be practiced otherwise than as specifically described therein.

The invention claimed is:

1. A chlorosilylarylgermane of formula (I):

where X=Y or X=[—Ge(Y$_2$)—SiCl$_3$] and
each Y is independently a phenyl group.

2. The chlorosilylarylgermane according to claim 1, which is selected from the group consisting of trichlorosilyltriphenylgermane and 1,2-bis(trichlorosilyl)-1,1,2,2-tetraphenyldigermane.

3. A method for preparing the chlorosilylarylgermane according to claim 1, the method comprising:
    (a) dissolving an arylchlorogermane with hexachlorodisilane in a solvent and
    (b) reacting in the presence of a catalyst at a temperature of 5 to 40° C., wherein the aryl groups of the arylchlorogermane are each independently phenyl.

4. The method according to claim 3, wherein the reacting (b) is carried out at room temperature.

5. The method according to claim 3, wherein
    the arylchlorogermane is at least one selected from the group consisting of
    a triarylchlorogermane and a diaryldichlorogermane,
    a molar ratio of the triarylchlorogermane, when present, to hexachlorodisilane is 1:1, and
    a molar ratio of the diaryldichlorogermane, when present, to hexachlorodisilane is 1:2.

6. The method according to claim 3, wherein the arylchlorogermane is at least one selected from the group consisting of triphenylchlorogermane and diphenyldichlorogermane.

7. The method according to claim 3, wherein the solvent is dichloromethane.

8. The method according to claim 3, wherein the catalyst comprises a phosphonium chloride [R$_4$P]Cl or an ammonium chloride salt [R$_4$N]Cl, where each R is independently Me, Et, iPr, nBu, Ph.

9. The method according to claim 3, wherein the catalyst is used in an amount of 0.001 to 1 mol per mole of hexachlorodisilane.

10. The method according to claim 3, wherein at least 5 mol of the solvent is used per mole of hexachlorodisilane.

11. The method according to claim 3, wherein
the reacting (b) is carried out with thorough mixing and over a period of 1 to 24 hours,
the solvent is subsequently removed, and
the chlorosilylarylgermane is obtained as a crystalline product.

12. A method for generating a GeSi layer, the method comprising:
preparing the GeSi layer from the chlorosilylarylgermane according to claim 1.

13. A method for preparing trichlorosilyltrichlorogermane, the method comprising:
dissolving $GeCl_4$ with hexachlorodisilane in a solvent and reacting in the presence of a catalyst at a temperature of 5 to 40° C.

14. A method for generating a GeSi layer, the method comprising:
preparing the GeSi layer from trichlorosilyltrichlorogermane obtained by the method according to claim 13.

* * * * *